US00PP14911P2

(12) United States Plant Patent
de Jong

(10) Patent No.: US PP14,911 P2
(45) Date of Patent: Jun. 15, 2004

(54) HYPERICUM PLANT NAMED 'KOLMBLAC'

(50) Latin Name: *Hypericum inodorum*
Varietal Denomination: Kolmblac

(75) Inventor: Jan de Jong, Heelsum (NL)

(73) Assignee: Gebr. Kolster BV, Boskoop (NL)

( * ) Notice: Subject to any disclaimer, the term of this patent is extended or adjusted under 35 U.S.C. 154(b) by 0 days.

(21) Appl. No.: 10/421,312

(22) Filed: Apr. 23, 2003

(51) Int. Cl.[7] ..... A01H 5/00
(52) U.S. Cl. ..... Plt./226
(58) Field of Search ..... Plt./226

(56) References Cited

PUBLICATIONS

UPOV ROM GTITM Computer Database, GTI JOUVE Retrieval Software 2003/05 citations for 'Kolmblac'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Hypericum plant named 'Kolmblac', characterized by its upright outwardly spreading plant habit; dark green leaves; dark brownish red-colored fruits that become almost black in color with development; and good postproduction longevity.

2 Drawing Sheets

Botanical classification/cultivar designation: *Hypericum inodorum* cultivar Kolmblac.

BACKGROUND OF THE INVENTION

The present Invention relates to a new and distinct cultivar of Hypericum plant, botanically known as *Hypericum inodorum,* commercially used as cut stems with fruits, and hereinafter referred to by the name 'Kolmblac'.

The new Hypericum is a product of a planned breeding program conducted by the Inventor in Wageningen, The Netherlands. The objective of the breeding program was to develop cut Hypericum varieties with attractive fruit coloration.

The new cultivar originated from a cross made by the Inventor in 1999 of two unidentified proprietary seedling selections, not patented. The cultivar Kolmblac was discovered and selected by the Inventor in 2000 as a flowering plant within the progeny of the stated cross in a controlled environment in Wageningen, The Netherlands.

Asexual reproduction of the new Hypericum by terminal cuttings taken at Boskoop, The Netherlands, has shown that the unique features of this new Hypericum are stable and reproduced true to type in successive generations of asexual reproduction.

SUMMARY OF THE INVENTION

The following traits have been repeatedly observed and are determined to be the unique characteristics of 'Kolmblac'. These characteristics in combination distinguish 'Kolmblac' as a new and distinct cultivar:

1. Upright and outwardly spreading plant habit.
2. Dark green leaves.
3. Dark brownish red-colored fruits that become almost black in color with development.
4. Good postproduction longevity.

Plants of the new Hypericum differ from plants of the parent seedling selections primarily in fruit coloration.

Plants of the new Hypericum can be compared to plants of the Hypericum cultivar Excellent Flair, not patented. In side-by-side comparisons conducted in Boskoop, The Netherlands, plants of the new Hypericum differed from plants of the cultivar Excellent Flair in the following characteristics:

1. Plants of the new Hypericum had darker colored fruits than plants of the cultivar Excellent Flair.
2. Fruits of plants of the new Hypericum were glossier than fruits of plants of the cultivar Excellent Flair.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph at the top of the first sheet comprises a side perspective view of a typical plant of 'Kolmblac'.

The photograph at the bottom of the first sheet is a close-up view of a typical stem and leaves of 'Kolmblac'.

The photograph at the top of the second sheet is a close-up view of typical flowers and developing fruits of 'Kolmblac'.

The photograph at the bottom of the second sheet is a close-up view of typical developed fruits of 'Kolmblac'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about two years old. The photographs and description were taken during the summer when outdoor day temperatures ranged from 14 to 30° C. and day temperatures ranged from 7 to 14° C. In the following description, color references are made to The Royal Horticultural Society Colour Chart, 2001 Edition, except where general terms of ordinary dictionary significance are used.

Botanical classification: *Hypericum inodorum* cultivar Kolmblac.

Parentage:

*Female parent.*—Unidentified proprietary selection of *Hypericum inodorum,* not patented.

*Male parent.*—Unidentified proprietary selection of *Hypericum inodorum,* not patented.

Propagation:

*Type.*—Terminal cuttings.

*Time to produce a rooted cutting.*—About 30 days at 20° C.

*Root description.*—Freely branching; medium thickness; brownish green in color.

Plant description:

*Plant form.*—Upright and outwardly spreading perennial woody shrub; globular.

*Growth habit.*—Moderately vigorous. Freely basal branching; dense and bushy growth habit.

*Plant height.*—About 55 cm.

*Plant width* (*spread*)—About 70 cm.

*Quantity of stems per year.*—About 15.

*Lateral branches.*—Length: About 10 cm. Diameter: About 2 mm. Internode length: About 2.6 cm. Strength: Moderate. Texture: Smooth; glabrous. Color, upper surface: 175A. Color, lower surface: 143A to 143B.

*Foliage description.*—Leaves opposite; single; sessile and generally symmetrical. Length: About 5.5 cm. Width: About 3.6 cm. Shape: Ovate. Apex: Obtuse to acute. Base: Obtuse. Margin: Entire. Texture: Glabrous; slightly rugose. Venation pattern: Pinnate. Color: Developing leaves, upper surface: 143A to 143B. Developing leaves, lower surface: 143B to 143C. Fully expanded leaves, upper surface: 139A. Fully expanded leaves, lower surface: 137D to 138A. Venation, upper and lower surfaces: 144C.

Flower description:

*Flower type and habit.*—Bright yellow single flowers arranged in terminal compound umbels with about eleven flowers per umbel. Flower not fragrant. Flower not persistant Flowers upright.

*Natural flowering season.*—Summer, typically July and August in Boskoop, The Netherlands; flowering period typical lasts about 60 days.

*Postproduction longevity.*—Cut flowers are typically harvested when all flowers have developed fruits. Postproduction longevity of cut stems with fruits is about two weeks.

*Inflorescence height.*—About 2.8 cm.

*Inflorescence diameter.*—About 4.1 cm.

*Flower buds.*—Height: About 8 mm. Diameter: About 1 cm. Shape: Ovoid. Color: 13A; towards apex, 17B.

*Flowers.*—Diameter: About 1.9 cm. Depth: About 1.9 cm.

*Petals.*—Quantity per flower: Five. Length: About 1 cm. Width: About 7.5 cm. Shape: Obovate. Aspect: Concave. Apex: Obtuse to acute. Base: Attenuate. Margin: Entire. Texture, upper and lower surfaces: Smooth; glabrous. Color: Developing and fully expanded petals, upper surface: 13A; towards the base 12A; color does not fade with subsequent development. Developing and fully expanded petals, lower surface: 13A; towards the base, 13B.

*Sepals.*—Quantity per flower: Five. Length: About 6 mm. Width: About 4 mm. Shape: Ovate to elliptic. Aspect: Reflexed. Apex: Obtuse to acute. Base: Broadly cuneate. Margin: Entire. Texture, upper and lower surfaces: Smooth, glabrous. Color: Developing sepals, upper and lower surfaces: 138B; towards the base and apex, tinged with 183C. Fully expanded sepals, upper surface: 138B; towards the base and apex, tinged with 183C. Fully expanded sepals, lower surface: 138C; towards the base and apex, tinged with 183C.

*Peduncles.*—Length: About 1 cm. Diameter: About 1 mm. Orientation: Erect to about 60° from vertical. Strength: Moderately strong. Color: 175B to 175C.

*Pedicels.*—Length: About 9 mm. Diameter: About 1 mm. Orientation: Erect to about 60° from vertical. Strength: Moderately strong. Color: 143B; overlain with 175C.

*Reproductive organs.*—Stamens: Quantity per flower: About 85. Stamen length: About 1.1 cm. Filament color: 13A. Anther shape: Broadly ovate. Anther length: About 0.5 mm. Anther color: 14C. Pollen amount: Moderate. Pollen color: 13A to 13B. Pistils: Quantity per flower: Three. Pistil length: About 4 mm. Stigma shape: Globular. Stigma color: Close to 178B to 178C. Style length: About 3.8 mm. Style color: 150C. Ovary color: 1B.

*Fruits.*—Quantity per flower: One. Days to ripening: About 25. Longevity on the plant: About 30 days. Type: Capsule. Shape: Ellipsoidal. Length: About 1.5 cm. Diameter: About 1 cm. Texture: Smooth; glabrous. Color, when developing: 187A; towards the base, 183A. Color, fully developed: Close to 202A.

*Seeds.*—Quantity per fruit: More than 100. Length: About 0.8 mm. Diameter: About 0.5 mm. Texture: Smooth; glabrous. Color: 199A to N199A.

Disease/pest resistance: Plants of the new Hypericum have not been observed to be resistant to pathogens and pests common to Hypericum.

Temperature tolerance: Plants of the new Hypericum have been observed to tolerate temperatures ranging from −15 to 35° C.

It is claimed:

1. A new and distinct cultivar of Hypericum plant named 'Kolmblac', as illustrated and described.

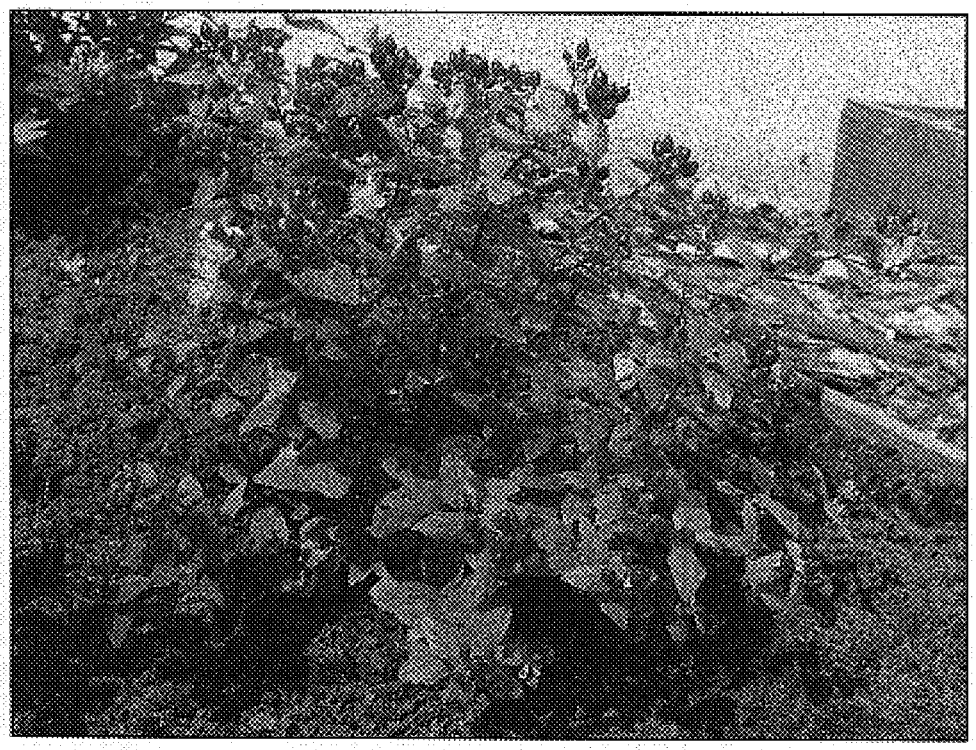
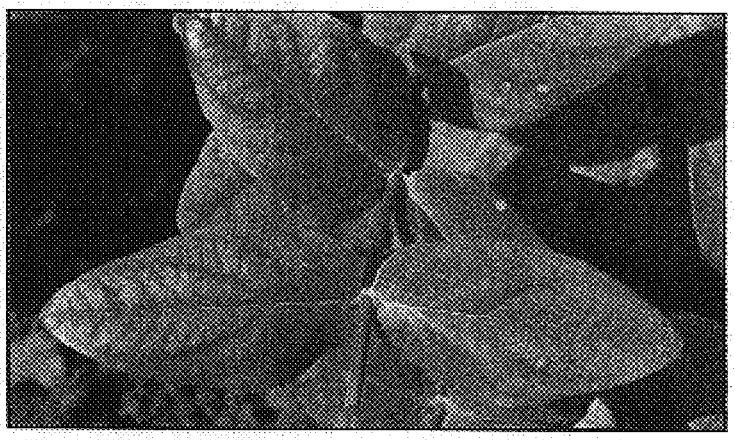

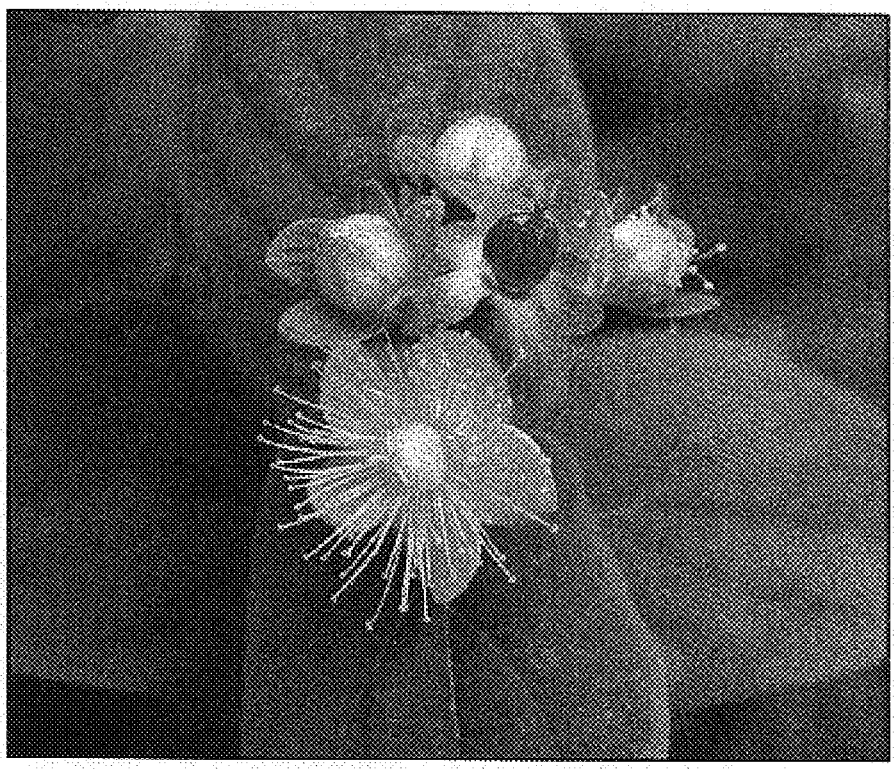
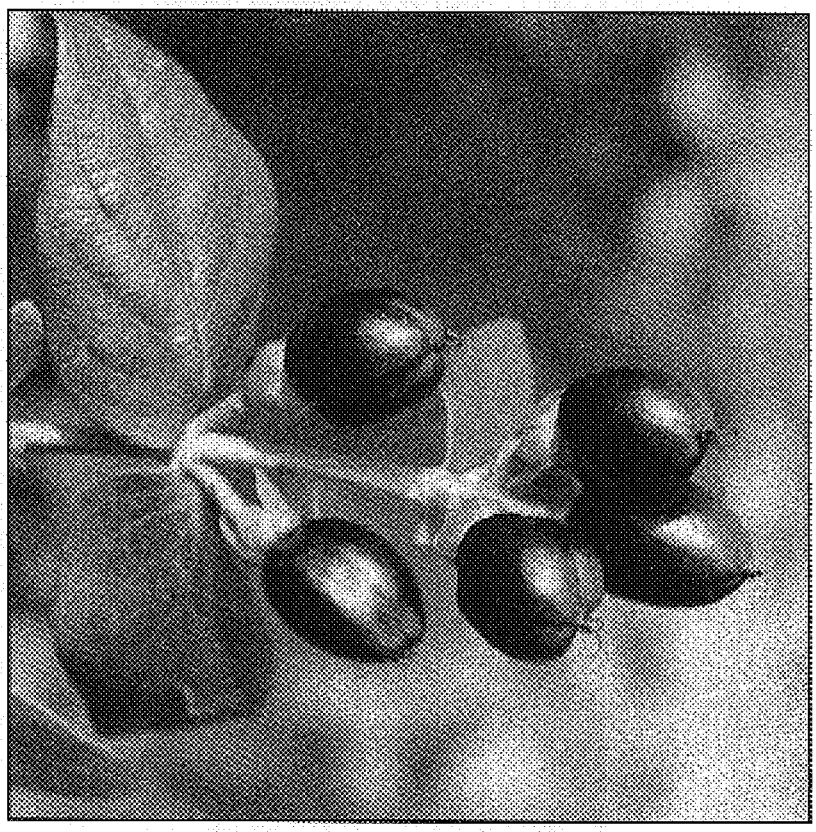

* * * * *